(12) United States Patent
Dennerlein et al.

(10) Patent No.: US 8,942,345 B2
(45) Date of Patent: Jan. 27, 2015

(54) METHOD FOR OBTAINING A 3D IMAGE DATASET OF AN OBJECT OF INTEREST

(75) Inventors: Frank Dennerlein, Forchheim (DE); Oliver Hornung, Fürth (DE); Markus Kowarschik, Langenzenn (DE)

(73) Assignee: Siemens Aktiengesellschaft, Munich (DE)

( * ) Notice: Subject to any disclaimer, the term of this patent is extended or adjusted under 35 U.S.C. 154(b) by 273 days.

(21) Appl. No.: 13/363,668

(22) Filed: Feb. 1, 2012

(65) Prior Publication Data

US 2012/0201352 A1 Aug. 9, 2012

(30) Foreign Application Priority Data

Feb. 4, 2011 (DE) .......................... 10 2011 003 653

(51) Int. Cl.
*G01N 23/04* (2006.01)
*A61B 6/03* (2006.01)
*G01D 18/00* (2006.01)
*A61B 6/00* (2006.01)
*G06T 11/00* (2006.01)
*A61B 6/02* (2006.01)

(52) U.S. Cl.
CPC .............. *G01N 23/046* (2013.01); *A61B 6/032* (2013.01); *A61B 6/035* (2013.01); *A61B 6/583* (2013.01); *G01N 2223/3303* (2013.01); *A61B 6/027* (2013.01); *A61B 6/4452* (2013.01); *A61B 6/4458* (2013.01); *A61B 6/584* (2013.01); *G06T 11/005* (2013.01)
USPC .............. 378/62; 378/196; 378/197; 378/207

(58) Field of Classification Search
CPC .......... A61B 6/027; A61B 6/03; A61B 6/032; A61B 6/305; A61B 6/4441; A61B 6/4452; A61B 6/4458; A61B 6/583; A61B 6/584; G01N 23/046; G01N 2223/3303; G06T 11/005
USPC ................. 378/18, 62, 91, 196, 197, 205, 207
See application file for complete search history.

(56) References Cited

U.S. PATENT DOCUMENTS 5,951,475 A * 9/1999 Gueziec et al. ................ 600/425
5,963,612 A * 10/1999 Navab ............................... 378/4

(Continued)

OTHER PUBLICATIONS

Siemens AG, Feb. 2008, "Introducing Artis zeego. The multi-axis system for Interventional Radiology. Are you ready to zee the future?" Siemens AG, Feb. 2008, pp. 1-12. Order No. A91AX-20805-11C2-7600, Druckzeichen: CC AX 20805 WS 02085.

(Continued)

*Primary Examiner* — Allen C. Ho

(57) ABSTRACT

A method for obtaining a 3D image dataset of an object of interest is proposed. A plurality of 2D X-ray images are captured and a 3D reconstruction is carried out using filtered back projection. The projection parameters have been measured with the aid of a calibrating phantom, possibly using an interpolation or extrapolation of such measurements. A model of effect strings of the components in an X-ray imaging device is obtained, and the model parameters are identified based on imaging of a calibrating phantom. A projection matrix can then be calculated for any positions on any desired trajectories, without having to use imaging of a calibrating phantom at precisely that position and desired trajectory.

6 Claims, 5 Drawing Sheets

(56) References Cited

U.S. PATENT DOCUMENTS

| | | | |
|---|---|---|---|
| 6,038,282 A * | 3/2000 | Wiesent et al. | 378/62 |
| 6,044,132 A * | 3/2000 | Navab | 378/163 |
| 6,049,582 A * | 4/2000 | Navab | 378/4 |
| 6,173,030 B1 * | 1/2001 | Patch | 378/4 |
| 6,200,024 B1 * | 3/2001 | Negrelli | 378/197 |
| 6,317,478 B1 * | 11/2001 | Patch | 378/4 |
| 6,333,631 B1 * | 12/2001 | Das et al. | 324/326 |
| 6,435,715 B1 | 8/2002 | Betz | |
| 6,731,283 B1 * | 5/2004 | Navab | 345/424 |
| 6,869,217 B2 * | 3/2005 | Rasche et al. | 378/197 |
| 7,455,453 B2 * | 11/2008 | Lauritsch et al. | 378/195 |
| 7,500,782 B2 * | 3/2009 | Klingenbeck-Regn et al. | 378/197 |
| 7,500,783 B2 * | 3/2009 | Kalender | 378/197 |
| 7,500,784 B2 * | 3/2009 | Grebner et al. | 378/198 |
| 7,515,677 B2 * | 4/2009 | Zellerhoff | 378/4 |
| 7,530,739 B2 * | 5/2009 | Lurz et al. | 378/198 |
| 7,559,694 B2 | 7/2009 | Berger | |
| 7,780,351 B2 * | 8/2010 | Heigl et al. | 378/207 |
| 7,789,562 B2 * | 9/2010 | Strobel | 378/207 |
| 7,912,271 B2 * | 3/2011 | Hoppe et al. | 382/132 |
| 8,007,173 B2 * | 8/2011 | Paidi et al. | 378/207 |
| 8,104,958 B2 * | 1/2012 | Weiser et al. | 378/207 |
| 8,180,132 B2 * | 5/2012 | Gorges et al. | 382/131 |
| 8,459,867 B2 * | 6/2013 | Muller | 378/196 |
| 8,538,505 B2 * | 9/2013 | Brunner et al. | 600/428 |
| 8,548,629 B2 * | 10/2013 | Ortmaier et al. | 700/255 |

OTHER PUBLICATIONS

"Practical Methods of Optimization", published by John Wiley and Sons, ISBN-10:0471494631 (nur Einleitung); Book; 1987; pp. 1-3. (Relevancy of "Practical Methods of Optimization"—1 Page).

* cited by examiner

METHOD FOR OBTAINING A 3D IMAGE DATASET OF AN OBJECT OF INTEREST

CROSS REFERENCE TO RELATED APPLICATIONS

This application claims priority of German application No. 10 2011 003 653.9 filed Feb. 4, 2011, which is incorporated by reference herein in its entirety.

FIELD OF INVENTION

The invention relates to a method for obtaining a 3D image dataset of an object of interest using an X-ray imaging device. The latter shall have a first effect string of components which are used to move an X-ray source, and there being in the X-ray imaging device a second effect string of components which are used to move an X-ray detector. The two effect strings are in general partly identical to one another, which will be assumed in the following.

BACKGROUND OF INVENTION

For example, the X-ray imaging device can comprise a six axis articulated aim robot which, downstream of a plurality of arms, has a hand which carries the X-ray source and the X-ray detector, said X-ray source and X-ray detector each being movable separately relative to the hand.

A 3D reconstruction is a method for obtaining a 3D image dataset in which grayscale values are assigned to volume elements of the three-dimensional space occupied (at least partly) by the object of interest. The grayscale values indicate the degree of attenuation of the X-radiation by the object of interest in the region of the respective volume element.

To obtain a 3D-image dataset using a 3D reconstruction, a sequence of two-dimensional X-ray images is taken. These are also known as projections because the object of interest is projected onto the plane of the X-ray detector using an X-ray source assumed to be virtually a point source. For example, by means of what is known as the (filtered) back projection process, contributions to the grayscale values can then be calculated for the volume elements. For back projection it is necessary to know the mapping rule from the X-ray source onto the X-ray detector. The mapping rule is usually specified as a so-called projection matrix.

X-ray imaging devices of simple construction have only a few degrees of freedom as regards the movement of the X-ray source and X-ray detector. The parameters for these degrees of freedom are run through systematically and image recordings of a calibrating object, known as a calibrating phantom, are made at a plurality of positions. For a known appearance and known location of the calibrating phantom, the projection matrix can be calculated for a respective position on the basis of these image recordings.

More modern X-ray imaging devices, such as those with a six axis articulated arm robot, have such a large number of degrees of freedom that it is no longer possible to run systematically through every combination of parameters of the individual components. This problem is overcome using interpolation or extrapolation in respect of the projection parameters in the projection matrices. However, the results thus obtained are unsatisfactory, the 3D reconstructions being of a less than desirable quality.

SUMMARY OF INVENTION

The object of the invention is therefore to specify a method for obtaining a 3D image dataset of an object of interest using an X-ray imaging device of the type specified in the introduction which for any utilization of the available degrees of freedom for obtaining the projections, i.e. for any trajectories, produces a higher quality of the 3D image dataset without having to calibrate individually for each trajectory.

This object is achieved by a method having the features as claimed in the claims.

The method first comprises the step a) of obtaining a model for at least one of the effect strings, a plurality of parameters being defined for said model. In step b), 2D X-ray images of a calibrating object are captured, i.e. corresponding imaging steps are automatically performed, possibly in response to an operator input. In step c), the model parameters are determined on the basis of the X-ray images acquired in step b). This so-called identification can be performed using conventional algorithms of the kind well known from the field of mathematical optimization.

Subsequently, in accordance with feature d) a desired trajectory is defined for at least one selected element of X-ray source and X-ray detector. The desired trajectory can be one that was not traversed when acquiring the two-dimensional X-ray images of the calibrating object. In particular, the desired trajectory can be any trajectory. In step e), the components of the effect string to the selected element are adjusted such that a sequence of positions is run through according to the desired trajectory. Then (feature point f)) 2D X-ray images of the object of interest are acquired, namely at each position of the sequence of positions. In step g), a trajectory for the element not selected is then defined or determined. Whether this trajectory is defined or determined depends on the number of degrees of freedom provided by the components of the X-ray imaging device. If the desired trajectory is defined using all the degrees of freedom of the X-ray imaging device, the desired trajectory for the element not selected follows automatically and must therefore merely be determined. The determining can take place before, after or simultaneously with steps e) and f). If there are remaining degrees of freedom for the movement of the element not selected, the trajectory can then be defined still further. This defining must take place in conjunction with feature point d), i.e. prior to steps e) and f). At feature point h), a subsequent step, the imaging parameters are calculated for each of the sequence of positions on the basis of the trajectories for the selected and the unselected element. In other words, the projection matrices can be calculated if it is known on the basis of the desired trajectory how the X-ray source was positioned at each capture of a 2D X-ray image, and if it is simultaneously known how the X-ray detector was positioned. Because the imaging parameters are now known, they can then be used in step i) to calculate the 3D image dataset (e.g. by filtered back projection), and precisely on the basis of the 2D X-ray images acquired in step f).

The method according to the invention therefore no longer involves using the calibrating phantom to determine projection matrices in advance for predetermined positions or rather combinations of values for the adjustment parameters of the components of the X-ray imaging device. Rather the calibrating phantom is merely used to ensure that the model parameters are known, and the obtained model with model parameters thus determined is then used, for any desired trajectories which are traversed during imaging of the object of interest, to calculate the projection matrices (imaging parameters) specifically in each case and then make further use thereof.

In a preferred embodiment of the method according to the invention, in step a) a model is obtained for both effect strings. The trajectory for the unselected element is then determined using the two models on the basis of the desired trajectory. If two models are immediately used, namely a model for each of the effect strings, the method according to the invention can be used on the basis of the modeling alone such that the imaging parameters can be determined precisely.

In a variant of this preferred embodiment, adjustment parameters for the components are calculated using an inverse model for the selected element. If the model specifies how particular adjustment parameters, i.e. positions of particular components, affect the location and the orientation of the X-ray source or X-ray detector, as the case may be, the adjustment parameters can be inferred from the position of the respective element by means of the inverse model. These can then also be moved to, i.e. implemented. If all the degrees of freedom are utilized, the trajectory for the unselected element can be calculated from these adjustment parameters. If not all the degrees of freedom are utilized, yet more adjustment parameters could be defined. The trajectory for the unselected element is then calculated from all the adjustment parameters.

In the second variant of the preferred embodiment, adjustment parameters for a movement described by a portion of the degrees of freedom, e.g. a translatory movement of the X-ray source and, simultaneously, adjustment parameters for a movement described by another portion of the degrees of freedom, e.g. a rotatory movement of the X-ray detector, are calculated using an inverse model. The term trajectory here therefore includes, in respect of the X-ray source, only part of the complete information (in the example, translatory information), in respect of the X-ray detector other (in the example, rotatory) information; combining steps d) and g) there are therefore effectively two desired trajectories.

Instead of using two models, determining the trajectory for the unselected element can include determining a relative position of the X-ray detector with respect to the X-ray source on the basis of the images captured in step f). Here an outline of a predetermined object is preferably mapped in step f). Because of the degree of distortion of this outline, e.g. the outline of an aperture allowing passage of the X-rays, the relative position of the X-ray detector with respect to the X-ray source can then be inferred. In this variant, the desired trajectory will preferably be defined for the X-ray source and the trajectory subsequently determined for the X-ray detector, but this can basically also be done the other way round.

BRIEF DESCRIPTION OF THE DRAWINGS

Preferred embodiments of the invention will now be described with reference to the accompanying drawings in which.

DETAILED DESCRIPTION OF INVENTION

Figure 1:
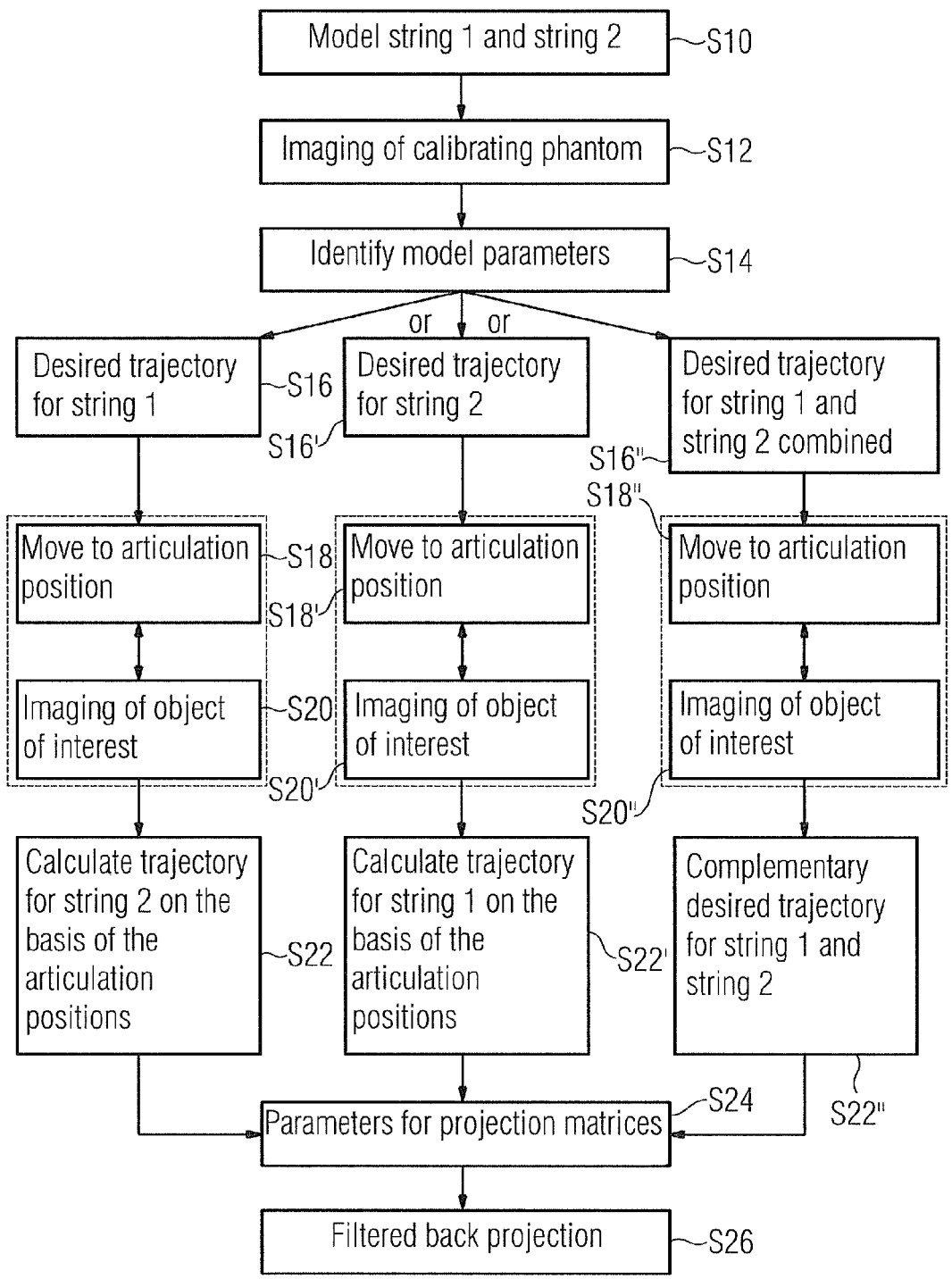
FIG. 1 shows a flowchart to explain two related variants of the method according to the invention.

The method according to the invention explained with reference to FIG. 1 begins in a variant group in step S10 with obtaining a model of the X-ray imaging, namely in respect of a first string (string 1), e.g. for the X-ray source 12, and in respect of a second string (string 2) of components, e.g. for the X-ray detector 14.

Figure 2:
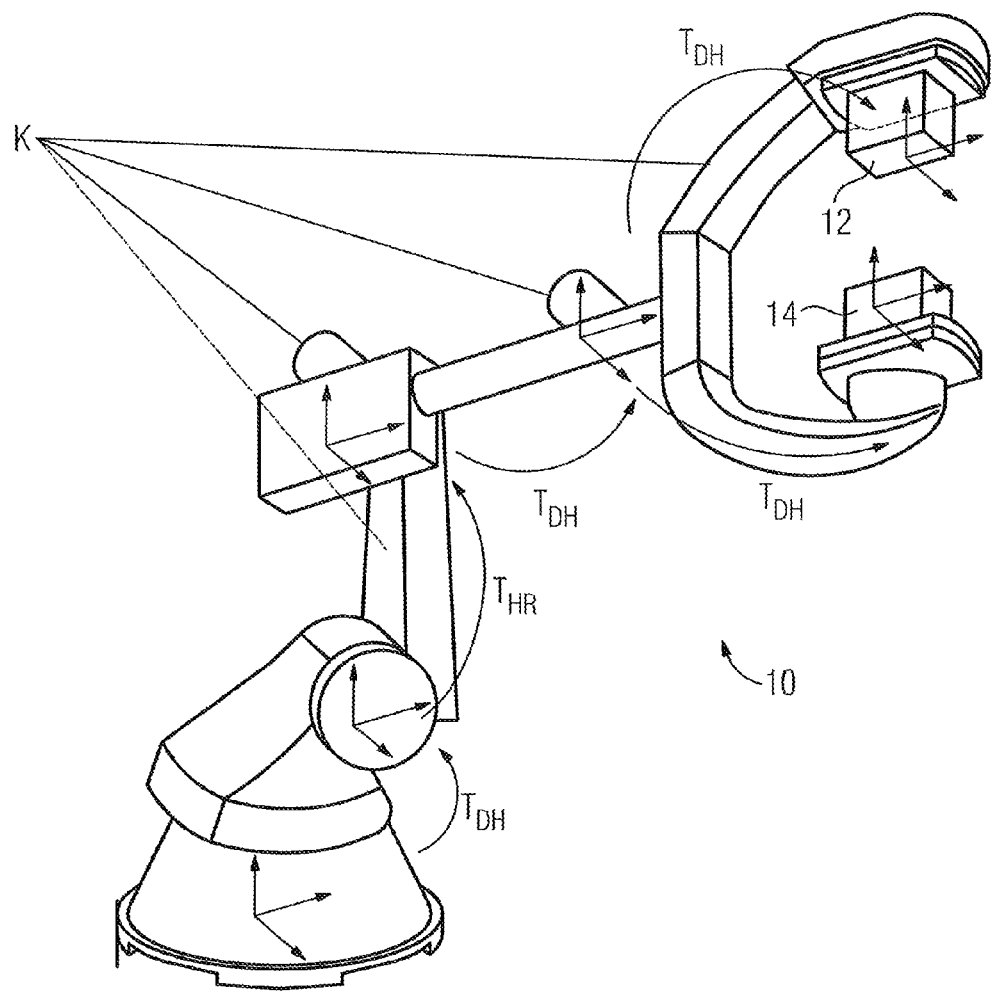
FIG. 2 shows a representation of the X-ray imaging device in which a method from FIG. 1 is used.

Such a model will be explained with reference to FIG. 2 which shows a six axis articulated arm robot 10 which carries the X-ray source 12 and the X-ray detector 14. For the per se known components of this X-ray imaging device, the parameters T and K of a model are now specified for kinematics and dynamics. The kinetic parameters can include Denavit-Hartenberg parameters, denoted by $T_{DH}$, and Hayati-Roberts parameters, denoted by $T_{HR}$.

The effect string for the X-ray source 12 therefore contains T and K parameters. The effect string for the X-ray detector 14 is virtually identical to the effect string for the X-ray source 12, but differs in at least one parameter.

When carrying out the method according to the invention, imaging of a calibrating phantom is now performed in step S12, i.e. a two-dimensional X-ray image is acquired at a plurality of positions of X-ray source 12 and X-ray detector 14. In step S14, the model parameters of the two models in respect of string 1 and string 2 can be identified on the basis of this plurality of two-dimensional X-ray images. The identifying of model parameters is known per se, parameter identification, also known as mathematical optimization, being described e.g. in the book "Practical Methods of Optimization", published by John Wiley and Sons, ISBN-10: 0471494631.

Now that the model is completely known, namely all the model parameters have been identified, in a first variant of the method according to the invention the desired trajectory for string 1, i.e. for the X-ray source 12, is defined in step S16. Via a trajectory, it can here be specified which translatory and rotatory movements the X-ray source 12 is to execute. Six degrees of freedom are thereby utilized, i.e. all the degrees of freedom available to a six axis articulated arm robot 10. On the basis of the desired trajectory, the inverse model for string 1 can now be used to calculate which adjustment parameters must be executed for the individual components of the six axis articulated arm robot 10, i.e. the positions to which the individual articulations of the device must be moved. This movement to the articulation positions then takes place in step S18. As a trajectory includes a plurality of positions for string 1, the articulation positions are moved to a plurality of times in step S18. A three-dimensional X-ray image of the object of interest is acquired, the imaging of the object of interest in step S20 therefore taking place in a coordinated manner with moving to the articulation positions in step S18.

Now that a plurality of two-dimensional X-ray images have been acquired, the trajectory for the unselected string 2 is calculated in step S22. As in this first variant all the degrees of freedom have been utilized, the trajectory traversed by the X-ray detector 14 can be calculated. As, on the one hand, the desired trajectory for the X-ray source 12 and is known, on the other, the associated trajectory for the X-ray detector 14 has been calculated, both the absolute position of X-ray source 12 and X-ray detector 14 in space and their relative position is known, and in this way the parameters for projection matrices can be calculated in step S24. After the imaging of the object of interest in step S20, with the aid of these parameters filtered back projection, for example, can then be performed in step S26 and in this way a 3D reconstruction can be carried out to obtain a 3D image dataset for the object of interest.

In a second variant of the method described, the desired trajectory is not determined for string 1, i.e. the X-ray source 12, but for string 2, for the X-ray detector 14, see step S16'. Once again the positions can be moved to in step S18' and the images acquired in step S20', and in step S22' the trajectory is calculated not for string 2 as in step S22 but now for string 1, i.e. the trajectory of the X-ray source 12. In running through steps S16' to S22', the X-ray source 12 and X-ray detector 14 roles are therefore reversed as compared to steps S16 to S22.

In another variant of the method, only a trajectory for translation is specified as the desired trajectory for string 1, i.e. for the X-ray source 12, so that only three parameters are defined, and three other degrees of freedom are available in the case of the six axis articulated arm robot 10. Accordingly, aspects of the desired trajectory can likewise be specified for the X-ray detector 14 (string 2), in this case these are preferably rotatory parameters. The desired trajectory in step S16" is therefore combined. Once again individual positions in the desired trajectory are moved to; in step S18" an appropriate position is therefore moved to a plurality of times for each articulation, and imaging of the object of interest takes place simultaneously therewith in step S20".

Although there is no remaining string in this case, the complementary trajectory must be calculated, i.e. the rotatory portions for string 1 and the translatory for string 2, step 22'. The method then proceeds to step S24, after which the filtered back projection S26 is calculated in order to obtain the 3D image dataset.

Figure 3:
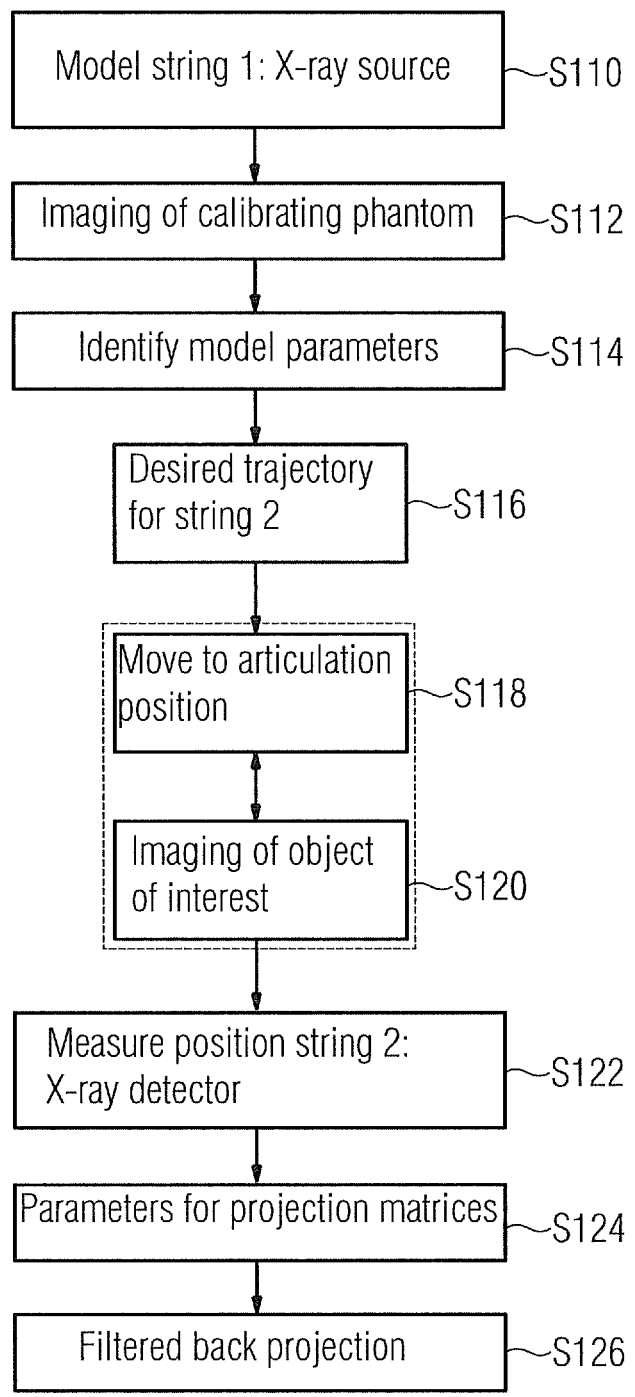
FIG. 3 shows a flowchart to explain another variant of the method according to the invention, FIG. 4 likewise illustrates an X-ray imaging device for this purpose.
Figure 4:
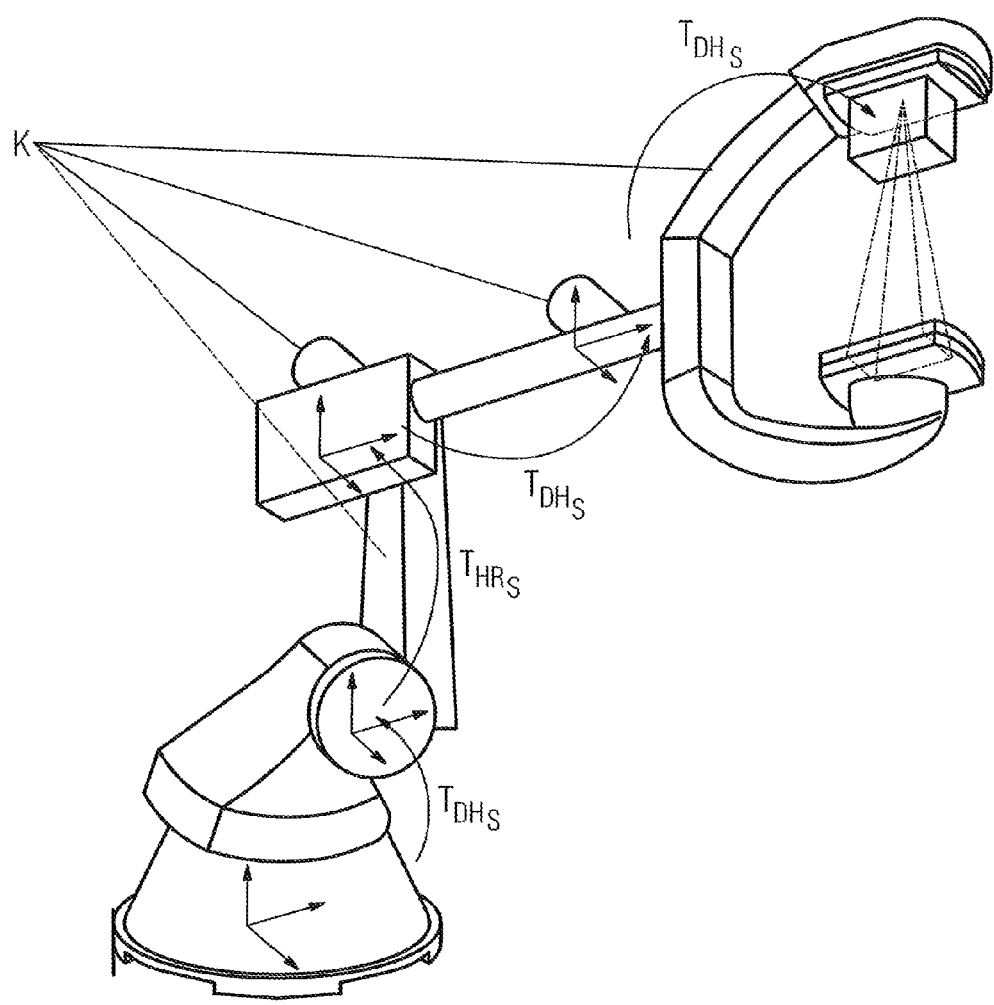
Figure 5:
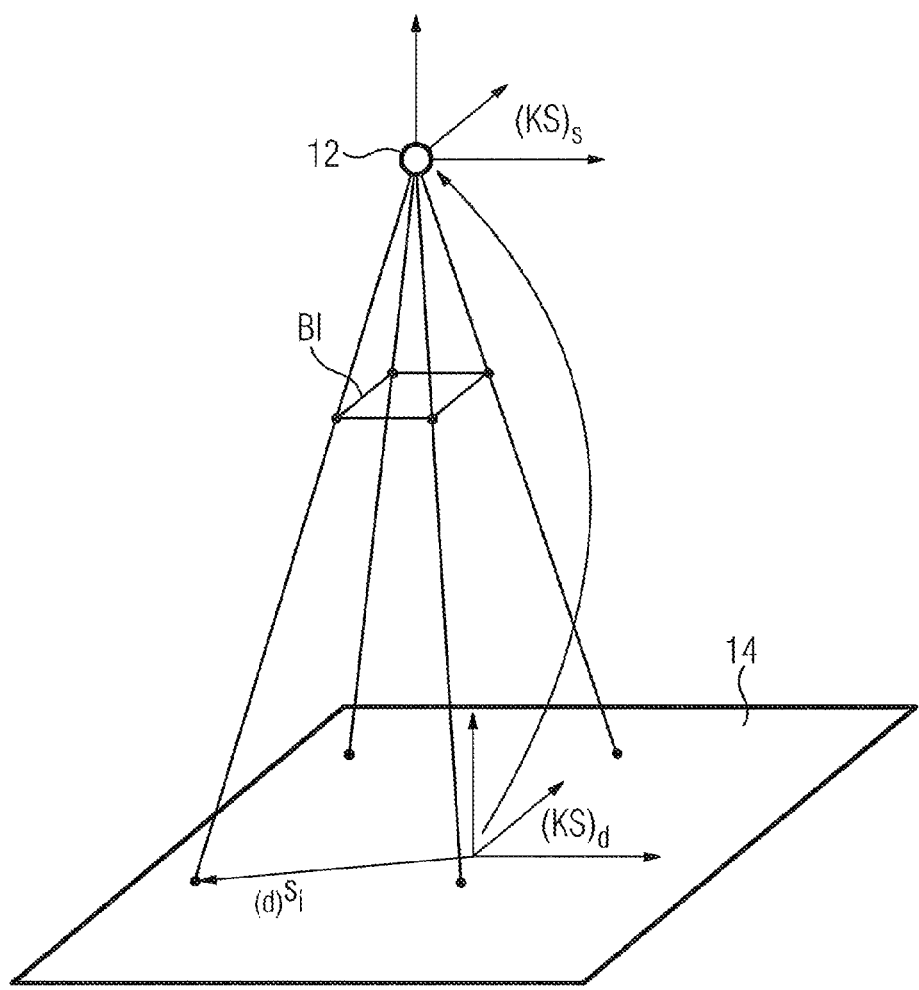
FIG. 5 shows a schematic illustrating the geometric relationships obtaining in FIG. 4.

In a variant of the method according to the invention explained below with reference to FIG. 3, only a model for one of the strings, in the example in the Figure only for the X-ray source 12, is obtained in step S110. The parameters T and K of the model are specified for kinematics and dynamics. The kinetic parameters for the X-ray source 12 can include Denavit-Hartenberg parameters, denoted by $T_{DH_S}$, and Hayati-Roberts parameters, denoted by $T_{HR_S}$. In step S112 the calibrating phantom is then imaged, i.e. a plurality of two-dimensional X-ray images are acquired, so that the model parameters can be subsequently identified in step S114. In step S116 the desired trajectory is now defined for string 1, i.e. for the X-ray source 12. As is known from S18 and S20 in FIG. 1, the articulation positions can now be moved to in step S118 (a plurality of times in each case) and an X-ray image is recorded in each case, i.e. overall imaging of the object of interest is acquired, see S120. As no calibrated model is now available for string 2, the trajectory for string 2 cannot now be calculated in step S22 as in FIG. 1. Instead, the position of string 2, i.e. the X-ray detector 14, is measured in step S122. This measurement is possible if, during imaging of the object of interest as per step S120, an appropriate outline is imaged at the same time, i.e. a rectangular aperture Bl, for example, see FIG. 5, is disposed in front of the X-ray source 12 which masks out so much X-radiation that unexposed areas remain on the X-ray detector 14. Depending on the location of the exposed areas on the X-ray detector 14, i.e. of the images produced by it, specified by the vectors (d) $s_i$ emanating from the origin of a coordinate system $(KS)_d$ of the X-ray detector 14, a different position of the X-ray detector 14 and therefore of the coordinate system $(KS)_d$ with respect to the coordinate system $(KS)_s$ of the X-ray source 12 can be specified. Typically the outline of a rectangular aperture Bl is both somewhat offset with respect to the origin, and also distorted, namely forming a trapezium, and because of the position and distortion, the relative position of the X-ray detector 14 with respect to the X-ray source 12 can then be calculated. Once this has taken place in step S122, the parameters for the projection matrices can be calculated in step S124 and then, in step S126 in the example, filtered back projection can be performed on the basis of the imaging acquired in step S122, so that even in this variant of the method a good 3D image dataset for the object of interest is obtained.

What is claimed is:

1. A method for obtaining a 3D image dataset of an object of interest using an X-ray imaging device having a first effect string of components which are used to move an X-ray source and having a second effect string of components which are used to move an X-ray detector, comprising:
    obtaining a model having a plurality of model parameters for at least one of the first effect string and the second effect string;
    capturing 2D X-ray images of a calibrating object using the X-ray imaging device;
    identifying the plurality of model parameters based on the 2D X-ray images;
    defining a desired trajectory for at least one selected element of the X-ray source and the X-ray detector;
    adjusting the components of the effect string of the at least one selected element of the X-ray source and the X-ray detector to run through a sequence of positions according to the desired trajectory using an articulated arm robot;
    capturing 2D X-ray images of the object of interest at each position of the sequence of positions using the X-ray imaging device;
    defining a trajectory for an unselected element of the X-ray source and the X-ray detector;
    calculating imaging parameters for the each position of the sequence of positions based on the trajectories for the at least one selected and the unselected elements; and
    calculating the 3D image dataset using the calculated imaging parameters based on the 2D X-ray images captured at the each position of the sequence of positions.

2. The method as claimed in claim 1, wherein obtaining a model having a plurality of model parameters for at least one of the first effect string and the second effect string comprising obtaining a first model for the first effect string and a second model for the second effect string; and wherein defining a trajectory for an unselected element of the X-ray source and the X-ray detector comprising determining the trajectory for the unselected element based on the first model, the second model, and the desired trajectory.

3. The method as claimed in claim 1, further comprising calculating adjustment parameters using an inverse model for the at least one selected element, wherein adjusting the components of the first effect string and the second effect string of the at least one selected element of the X-ray source and the X-ray detector comprising adjusting the components according to the adjustment parameters; and wherein defining a trajectory for an unselected element of the X-ray source and the X-ray detector comprising calculating the trajectory for the unselected element from the adjustment parameters.

4. The method as claimed in claim 3, wherein calculating adjustment parameters comprising calculating a first adjustment parameter for a movement of the X-ray source described by a portion of a possible degrees of freedom of the X-ray imaging device and a second adjustment parameter for a movement of the X-ray detector described by another portion of the possible degrees of freedom of the X-ray imaging device simultaneously using the inverse model.

5. The method as claimed in claim 1, wherein capturing 2D X-ray images of the object of interest at the each position of the sequence of positions comprising: determining a relative position of the X-ray detector with respect to the X-ray source based on the 2D X-ray images; and imaging an outline of the object.

6. The method as claimed in claim 1, further comprising calculating projection matrices for the 2D X-ray images of the calibrating object; and wherein identifying the plurality of model parameters based on the projection matrices.

* * * * *